United States Patent [19]

Morikawa et al.

[11] 3,932,550

[45] Jan. 13, 1976

[54] PROCESS FOR PRODUCTION OF 2,6-DIMETHYL-1,3,6-OCTATRIENE

[75] Inventors: Hiroyuki Morikawa; Takahiro Sato, both of Ibaraki, Japan

[73] Assignee: Mitsui Petrochemical Industries, Ltd., Japan

[22] Filed: Sept. 4, 1974

[21] Appl. No.: 503,162

[30] Foreign Application Priority Data

Sept. 8, 1973 Japan.............................. 48-101375

[52] U.S. Cl........................... 260/677 R; 260/666 A
[51] Int. Cl.²..................... C07C 11/00; C07F 1/02
[58] Field of Search....... 260/677 R, 683.15, 666 A, 260/677

[56] References Cited
UNITED STATES PATENTS

| | | | |
|---|---|---|---|
| 3,088,985 | 5/1963 | Wilke................ | 260/677 R |
| 3,219,716 | 5/1965 | Wittenberg et al............... | 260/666 |
| 3,228,917 | 1/1966 | Childers........................... | 260/84.1 |
| 3,372,206 | 3/1968 | Pruett et al........................ | 260/666 |
| 3,457,319 | 7/1969 | Olechowski et al............. | 260/677 R |
| 3,689,585 | 9/1972 | Morikawa....................... | 260/677 R |
| 3,707,581 | 12/1972 | Heckelsberg................... | 260/677 R |

FOREIGN PATENTS OR APPLICATIONS 2,063,038   7/1971   Germany....................... 260/677 R

*Primary Examiner*—Delbert E. Gantz
*Assistant Examiner*—Juanita M. Nelson
*Attorney, Agent, or Firm*—Robert E. Burns; Emmanuel J. Lobato; Bruce L. Adams

[57] ABSTRACT

A process for producing 2,6-dimethyl-1,3,6-octatriene by dimerizing isoprene in the presence of a novel catalyst composition, which comprises: (A) a zirconium component represented by the formula: $Zr(OR)_nCl_{4-n}$ wherein R is a chlorinated alkyl group containing two to 20 carbon atoms or a chlorinated cycloalkyl group containing three to 20 carbon atoms, and $n$ is an integer of 1 to 4; (B) an aluminum component represented by the formula: $AlR'_mCl_{3-m}$ wherein R' is an alkyl group containing one to 10 carbon atoms, a cycloalkyl group containing three to 10 carbon atoms, or an aryl group, and $m$ is 1.5 or 2; and (C) a coordinating component.

12 Claims, No Drawings

PROCESS FOR PRODUCTION OF 2,6-DIMETHYL-1,3,6-OCTATRIENE

BACKGROUND OF THE INVENTION

1. Field of the Invention

The present invention relates to a process for producing 2,6-dimethyl-1,3,6-octatriene by linear dimerization of isoprene. More particularly, it is concerned with the use of novel catalyst compositions comprising specific zirconium compounds, aluminum compounds, and coordinating compounds.

2. Description of the Prior Art

For producing 2,6-dimethyl-1,3,6-octatriene from isoprene, there have been proposed a method using Ziegler type catalysts wherein titanium compounds are used, as described in French Pat. No. 1,393,071, *Quarterly of the Government Industrial Research Institutes, Osaka*, 15, 271, *Makromol. Chem.*, 123, 274 (1969), etc., a method using vanadium based catalysts as described in Japanese Patent Laid Open No. 5704/1973, etc., and so on. In accordance with these methods, however, cyclic dimer, trimer and the like are by-produced and good results cannot be obtained.

Furthermore, as a method for selectively producing 2,6-dimethyl-1,3,6-octatriene, the use of zirconium based catalyst is described in *Bull. Chem. Soc. Japan*, 42, 2303 (1969), Japanese Patent Laid Open Nos. 34303/1972 and 5706/1973, etc., and the use of hafnium-based catalyst is described in *Bull. Chem. Soc. Japan*, 42, 1383 (1969), etc.

These catalysts, however, could incur certain problems, such as that the production thereof is, as described in *J. Chem. Soc.*, 1952, 2032 to 2035, etc., complicated in that ammonia is used as a dehydrochlorination agent, precipitated $NH_4Cl$ is filtered and washed as a post-treatment, and so on, and that conventional $Zr(OR)_4$ is readily hydrolyzed with the moisture contained in air and is polymerized into resinous compounds.

Furthermore, the use of these catalysts is industrially disadvantageous in that the catalyst cost is high because sufficient activity cannot be obtained unless a large amount of the catalyst is added to the monomer feed.

It has been previously found through our investigation of the oligomerization of isoprene by the use of a zirconium based catalyst that a zirconium alkoxychloride-based catalyst overcomes the above mentioned drawbacks (see U.S. Pat. No. 3,689,585, British Pat. No. 1,298,609, and Japanese Pat. Publication No. 104,020/1969).

As a result of further investigation of the improved catalyst, we have now discovered a novel catalyst which can be produced at much lower cost and much easier than conventional zirconium based catalysts.

SUMMARY OF THE INVENTION

Accordingly, an object of the present invention is to provide a novel catalyst composition which makes possible the production of 2,6-dimethyl-1,3,6-octatriene from isoprene in high yields and selectively.

Another object of the present invention is to provide a novel catalyst composition which is highly active at a low level of concentration.

A further object of the present invention is to provide a process for producing 2,6-dimethyl-1,3,6-octatriene from isoprene by the use of the novel catalyst composition.

Other objects, further features, and advantages of the present invention will become apparent from the following detailed description.

In accordance with the present invention, 2,6-dimethyl-1,3,6-octatriene is produced by dimerizing isoprene in the presence of a catalyst composition comprising (A) a zirconium component consisting of one or more compounds represented by the formula $Zr(OR)_nCl_{4-n}$ wherein R is a chlorinated alkyl group containing two to 20 carbon atoms or a chlorinated cycloalkyl group containing three to 20 carbon atoms, and $n$ is an integer of 1 to 4; (B) an aluminum component consisting of one or more compounds represented by the formula $AlR'_mCl_{3-m}$ wherein R' is an alkyl group containing one to 10 carbon atoms, a cycloalkyl group containing three to 10 carbon atoms or an aryl group, and $m$ is 1.5 or 2; and (C) a coordinating component.

DETAILED DESCRIPTION OF THE INVENTION

The catalyst compositions as used in the present invention are highly active at low concentration and make possible the production of 2,6-dimethyl-1,3,6-octatriene in high yields and selectively. Moreover, since the amount of the catalyst composition used is small, post-treatment such as decomposition of catalyst is substantially simplified. Thus, the present invention is industrially very advantageous.

1. Catalyst

A. Zirconium Component

The zirconium component of the catalyst composition as used in the present invention comprises one or more compounds represented by the formula $Zr(OR)_nCl_{4-n}$ wherein R is a chlorinated alkyl group containing two to 20 carbon atoms, or a chlorinated cycloalkyl group containing three to 20 carbon atoms, and $n$ is an integer of 1 to 4. Representative examples of the zirconium compounds are shown below.

Tetrachloroethoxy zirconium
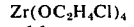
Tetrachloropropoxy zirconium
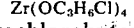
Tetrachlorobutoxyzirconium
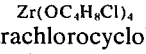
Tetrachlorocyclobutenoxyzirconium

Tetrachlorocyclohexoxyzirconium

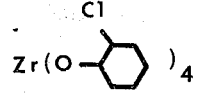

Chloroethoxytrichlorozirconium
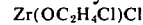
Chloropropoxytrichlorozirconium
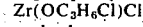
Chlorododecoxytrichlorozirconium
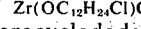
Chlorocyclododecoxytrichlorozirconium

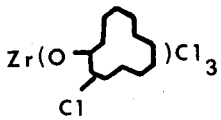

Chlorocyclobutoxytrichlorozirconium

Chlorocyclopentoxytrichlorozirconium

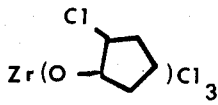

Di(chloropropoxy)trichlorozirconium
  Zr(OC₃H₅Cl₂)Cl₃
Di(chloroethoxy)dichlorozirconium
  Zr(OC₂H₄Cl)₂Cl₂
Di(chloropropoxy)dichlorozirconium
  Zr(OC₃H₆Cl)₂Cl₂
Di(chlorobutoxy)dichlorozirconium
  Zr(OC₄H₈Cl)₂Cl₂
Di(chlorocyclopentoxy)dichlorozirconium

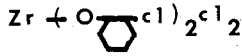

Di(chlorocyclohexoxy)dichlorozirconium

Di(chlorocyclooctoxy)dichlorozirconium

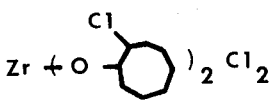

Tri(chloroethoxy)chlorozirconium
  Zr(OC₂H₄Cl)₃Cl
Tri(chloropropoxy)chlorozirconium
  Zr(OC₃H₆Cl)₃Cl
Tri(dichloropropoxy)chlorozirconium
  Zr(OC₃H₅Cl₂)₃Cl
Tri(chlorohexoxy)chlorozirconium

These zirconium chloroalkoxy compounds can be produced by reacting zirconium tetrachloride with the corresponding alkylene oxides by known methods as described in *Kogyo Kagaku Zasshi*, Vol. 71, No. 3, page 76(1968), and *J. Appl. Chem.*, 20, 183 to 187(1970). Since dehydrochlorination is not required and all the complicated steps are eliminated, they can be easily produced.

In the case of the reaction of zirconium tetrachloride and alkylene oxides, the reaction products possess a structure wherein at least one chlorine of the zirconium tetrachloride is substituted with the group

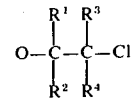

in which R¹ to R⁴ are substituents forming the alkylene oxide

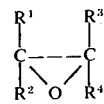

and at least one pair comprising two substituents selected from R¹, R², R³ and R⁴ (e.g., R¹ and R³) may combine to form a ring (in the case of, e.g., cyclohexeneoxide).

B. Aluminum Component

The aluminum component of the catalyst composition of the present invention comprises one or more compounds represented by the formula $AlR'_mCl_{3-m}$ where R' is an alkyl group containing one to 10 carbon atoms, a cycloalkyl group containing three to 10 carbon atoms, or an aryl group, and m is 1.5 or 2. Representative examples of the aluminum compounds are as follows.

Dimethylaluminum chloride
Diethylaluminum chloride
Diisobutylaluminum chloride
Diphenylaluminum chloride
Dioctylaluminum chloride
Methylaluminum sesquichloride
Ethylaluminum sesquichloride
Butylaluminum sesquichloride C. Coordinating Component As the coordinating component as used in the present invention, those compounds containing one or more, the same or different, non-covalent electron pairs such as oxygen, nitrogen, sulfur, phosphorus, and the like, and having a molecular weight less than about 1,000 or having carbon atoms of one to about 30 can be used. These compounds can be used alone or in admixtures comprising two or more thereof. Representative examples of the coordinating compounds are as follows.

Oxygen-containing compound
  Ethers: e.g., dimethyl ether, diethyl ether, ethyleneglycol dimethyl ether, phenyl glycidyl ether, tetrahydrofuran.
  Alcohols: e.g., methanol, ethanol, propanols, butanols, butanediol, ethyleneglycol monomethyl ether, benzyl alcohol.
  Ketones and aldehydes: e.g., acetone, methyl ethyl ketone, benzaldehyde, furfural, cyclohexanone.
  Siloxanes: e.g., dimethyldiethoxy silane, cyclohexamethyl trisiloxane.
Nitrogen-containing compound
  Amines: e.g., trimethylamine triethylamine, ethanolamines, pyridine, piperazine, dipyridyl.
  Amides: e.g., acetamide, benzamide, urea.

Nitriles: e.g., acetonitrile, benzonitrile.
Sulfur-containing compound
Mercaptans: e.g., methylmercaptan, ethylmercaptan, benzylmercaptan.
Sulfoxides: e.g., dimethylsulfoxide, sulfolane, sulfolene, dimethylsulfone.
Phosphorus containing compound
Phosphines: e.g., trimethylphosphine, triphenylphosphine.
Phosphates: e.g., trimethyl phosphate, tricresyl phosphate.
Phosphites: e.g., trimethyl phosphite, triphenyl phosphite.
Phosphineoxides: e.g., tributyl phosphineoxide, tricresyl phosphineoxide.

Composition of Catalyst

The proportions of the components as used in the present invention are important and preferably in the following ranges. When the proportions are unbalanced, catalyst activity tends to be reduced.

1. The quantity of the coordinating component (C) containing unpaired electron is an important factor controlling selectivity of 2,6-dimethyl-1,3,6-octatriene and polymerization of isoprene. The molar ratio of the coordinating component to the zirconium component (Zr) is preferably 0.01 to 10 ( (C)/(Zr) = 0.01 to 10 ) and more preferably, 0.1 to 2.0.

2. The quantity of the aluminum component can be changed in wide limits. In general, the molar ratio of the aluminum component (Al) to the zirconium component is 1 to 100 ( (Al)/(Zr) = 1 to 100 ) and preferably 3 to 30.

Preparation of Catalyst

The catalyst composition as used in the present invention can be produced by mixing the components, e.g., in a stream of inert gas or isoprene feed.

In accordance with the preferred preparation sequence, the zirconium compound and the coordinating compound are added to a solvent in this order and stirred, and then the aluminum compound is added, whereby an active catalyst composition can be obtained. It is preferred that the preparation temperature range from 30° to 80°C.

2. Catalytic Dimerization

Solvents which can be used in the present invention include aromatic hydrocarbons such as benzene, toluene, xylene, and the like, and aliphatic hydrocarbons such as hexane, heptane, and the like. The aromatic hydrocarbons which are convenient for dissolving the catalyst therein are preferred.

These solvents can be used alone or in admixtures comprising two or more thereof.

The reaction temperature can be changed within the range of 0° to 200°C, and the preferred range is 50° to 150°C. The reaction can be effected either at atmospheric pressure or under pressure.

The molar ratio of isoprene to the zirconium compound is 50 to 5,000, the preferred range being from 1,000 to 3,000. On the other hand, with conventional methods, e.g., the method of Japanese Patent Laid Open No. 5706/1973, the molar ratio is 5 to 1,000, the preferred range being from 50 to 500.

The following examples are given to illustrate preferred embodiments of the present invention.

EXAMPLES 1 to 7

After purging a 500-ml autoclave with nitrogen gas, the solvents, zirconium compounds, coordinating compounds and aluminum compounds as indicated in Table 1 were charged thereto in amounts as indicated in Table 1 and mixed at 40°C to produce respective catalysts.

Then, after charging 27 g of isoprene, the reaction mixtures were stirred at 110°C for 8 hours in the cases of Examples 1, 2, 4, 6 and 7, and at 130°C for 5 hours in the cases of Examples 3 and 5.

On adding methanol, the catalysts were decomposed and the products were separated by distillation. The fraction of 2,6-dimethyl-1,3,6-octatriene boiling at 50°–60°C under reduced pressure of 10–15 mmHg was obtained in quantities as shown in Table 1.

Table 1

| Example | Feed (g) | Solvent (ml) | Zirconium Compound (mM) | (g) | Coordinating Compound (mM) | (g) | Aluminum Compound (mM) | (g) | DMOT Fraction (g) | DMOT Yield (%) | DMOT Selectivity (%) |
|---|---|---|---|---|---|---|---|---|---|---|---|
| 1 | isoprene 27 | toluene 100 | tetrachloropropoxy zirconium 0.2 | 0.093 | triphenylphosphine 0.2 | 0.052 | diethylaluminum chloride 4.0 | 0.484 | 20.7 | 76.7 | 84.9 |
| 2 | " | " | tetrachloropropoxy zirconium 2.0 | 0.93 | triphenylphosphine 2.0 | 0.524 | diethylaluminum chloride 40.0 | 4.840 | 22.6 | 83.6 | 88.1 |
| 3 | " | " | chlorocyclobutenoxy trichlorozirconium 0.4 | 0.121 | furfural 0.4 | 0.038 | ethylaluminum sesquichloride 4.0 | 0.992 | 21.7 | 80.5 | 86.1 |
| 4 | " | xylene 100 | di(chlorobutoxy) dichlorozirconium 1.2 | 0.452 | monoethanolamine 0.6 | 0.037 | diethylaluminum chloride 6.0 | 0.726 | 19.5 | 72.2 | 78.8 |
| 5 | " | " | tri(dichloropropoxy) chlorozirconium 0.2 | 0.102 | sulfolane 0.4 | 0.048 | diisobutylaluminum chloride 4.0 | 0.708 | 21.3 | 78.8 | 82.9 |
| 6 | " | benzene 100 | chlorododecenoxy trichlorozirconium 0.8 | 0.334 | triphenylphosphine 0.4 | 0.105 | ethylaluminum sesquichloride 8.0 | 1.984 | 19.7 | 73.1 | 81.1 |
| 7 | " | " | tetrachloroethoxy zirconium 0.4 | 0.164 | cyclohexamethyl-trisiloxane 0.4 | 0.082 | diethylaluminum chloride 4.0 | 0.484 | 21.4 | 79.3 | 80.5 | mM : millimole
DMOT : 2,6-dimethyl-1,3,6-octatriene

COMPARISON EXAMPLE 1

The procedures of Examples 1 and 2 were repeated with the exception that the same quantity of tetrapropoxy zirconium was used in place of tetrachloropropoxy zirconium, and thus 2,6-dimethyl-1,3,6-octatriene (DMOT) was obtained. These results are shown in Tables 2 and 3.

Table 2

Comparison at low concentration of catalyst

| | Zirconium compound | Concentration of zirconium compound | Conversion of isoprene | DMOT selectivity | DMOT yield | DMOT/Zr |
|---|---|---|---|---|---|---|
| Example 1 | tetrachloropropoxy zirconium | 0.93 mg/c.c. solvent | 90.3% | 84.9% | 76.7% | 222.6g/g |
| Comparison example | tetrapropoxy zirconium | " | 30.1% | 70.1% | 21.1% | 61.3g/g |

Reaction condition: the same as in Example 1.

Table 3

Comparison at high concentration of catalyst

| | Zirconium compound | Concentration of zirconium compound | Conversion of isoprene | DMOT selectivity | DMOT yield | DMOT/Zr |
|---|---|---|---|---|---|---|
| Example 2 | tetrachloropropoxy zirconium | 9.3 mg/c.c. solvent | 94.9% | 88.1% | 83.6% | 24.3 g/g |
| Comparison example | tetrapropoxy zirconium | " | 90.2% | 80.0% | 72.2% | 21.0 g/g |

Reaction condition: the same as in Example 2.

As shown in Table 2, the catalyst compositions of the present invention exhibit high reactivity and selectivity at low concentration and possess capability to produce 2,6-dimethyl-1,3,6-octatriene in high yields.

That is, with the zirconium chloroalkoxide based catalyst of the present invention, the quantity of the product per unit of catalyst is markedly increased, whereas with the conventional zirconium alkoxide based catalyst, as shown in Table 3, good results comparable to those with the catalyst composition of the present invention cannot be obtained even at high concentration.

COMPARISON EXAMPLE 2

The procedure of Example 1 was repeated with the exception that triphenylphosphine was not used. The results are shown in Table 4.

Table 4

| | Quantity of coordinating compound used | DMOT selectivity | Polymer selectivity |
|---|---|---|---|
| Example | triphenylphosphine/zirconium compound = 1 | 84.9 % | 8.1 % |
| Comparison example 2 | none | 45.1 % | 30.0 % |

As shown in Table 4, an excessively small quantity of the coordinating compound reduces DMOT selectivity and increases polymer selectivity.

What is claimed is:

1. A process for producing 2,6-dimethyl-1,3,6-octatriene from isoprene which comprises dimerizing isoprene in the presence of a catalyst composition comprising: (A) a zirconium component selected from the group consisting of one or more compounds represented by the formula $Zr(OR)_n Cl_{4-n}$ wherein R is a chlorinated alkyl group containing two to 20 carbon atoms or a chlorinated cycloalkyl group containing three to 20 carbon atoms, and n is an integer of 1 to 4; (B) an aluminum component consisting of one or more compounds represented by the formula $AlR'_m Cl_{3-m}$ wherein R' is an alkyl group containing one to 10 carbon atoms, a cycloalkyl group containing three to 10 carbon atoms or an aryl group, and m is 1.5 or 2; and (C) a coordinating component selected from the group consisting of an oxygen-containing compound, a nitrogen-containing compound, a sulfur-containing compound, a phosphorus-containing compound, and mixtures thereof.

2. The process according to claim 1 wherein the molar ratio of the coordinating component to the zirconium component is 0.01 to 10.

3. The process according to claim 1, wherein the molar ratio of the aluminum component to the zirconium component is 1 to 100.

4. The process according to claim 1 wherein the oxygen containing compound is selected from the group consisting of ethers, alcohols, ketones, aldehydes, and siloxanes.

5. The process according to claim 1 wherein the nitrogen containing compound is selected from the group consisting of amines, amides, and nitriles.

6. The process according to claim 1 wherein the sulfur containing compound is selected from the group consisting of mercaptans and sulfoxides.

7. The process according to claim 1 wherein the phosphorus containing compound is selected from the group consisting of phosphines, phosphates, phosphites, and phosphineoxides.

8. The process according to claim 1 wherein the dimerization is effected in a hydrocarbon solvent.

9. The process according to claim 8 wherein the hydrocarbon solvent is selected from aromatic hydrocarbons.

10. The process according to claim 1 wherein the dimerization is effected at temperatures of 0° to 200°C.

11. The process according to claim 1 wherein the coordinating component is selected from the group consisting of tetrahydrofuran, benzyl alcohol, dimethylsulfoxide, trimethylphosphine, tricresylphosphine, triphenyl phosphite, and tricresylphosphine oxide.

12. The process according to claim 1 wherein the coordinating component is selected from the group consisting of triphenyl phosphine, furfural, monoethanol amine, sulfolane, and cycrohexamethyl trisiloxane.

* * * * *

UNITED STATES PATENT OFFICE
CERTIFICATE OF CORRECTION

PATENT NO. : 3,932,550
DATED : January 13, 1976
INVENTOR(S) : MORIKAWA et al

It is certified that error appears in the above-identified patent and that said Letters Patent are hereby corrected as shown below:

Change the assignee to read:

--Mitsubishi Petrochemical Company Limited--

Signed and Sealed this

*twenty-ninth* Day of *June 1976*

[SEAL]

Attest:

RUTH C. MASON
*Attesting Officer*

C. MARSHALL DANN
*Commissioner of Patents and Trademarks*